United States Patent [19]

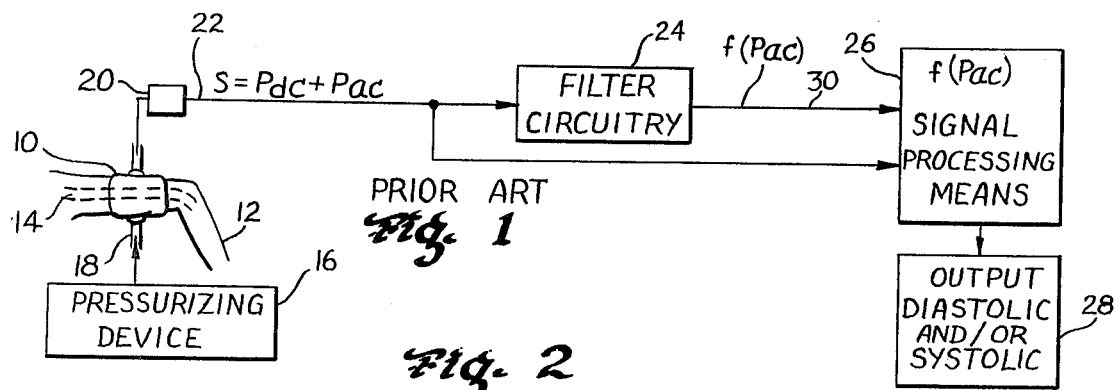
Fig. 1 PRIOR ART
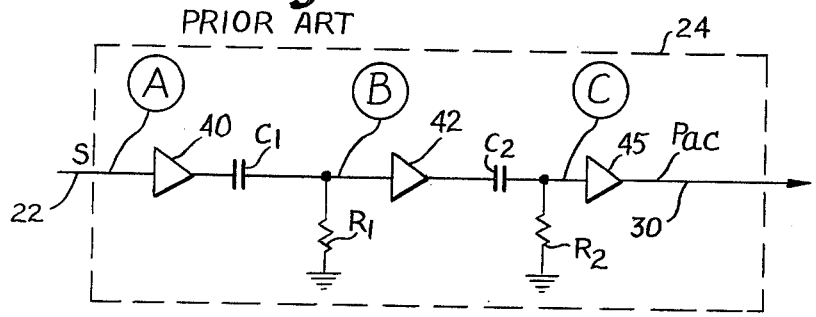
Fig. 2 PRIOR ART
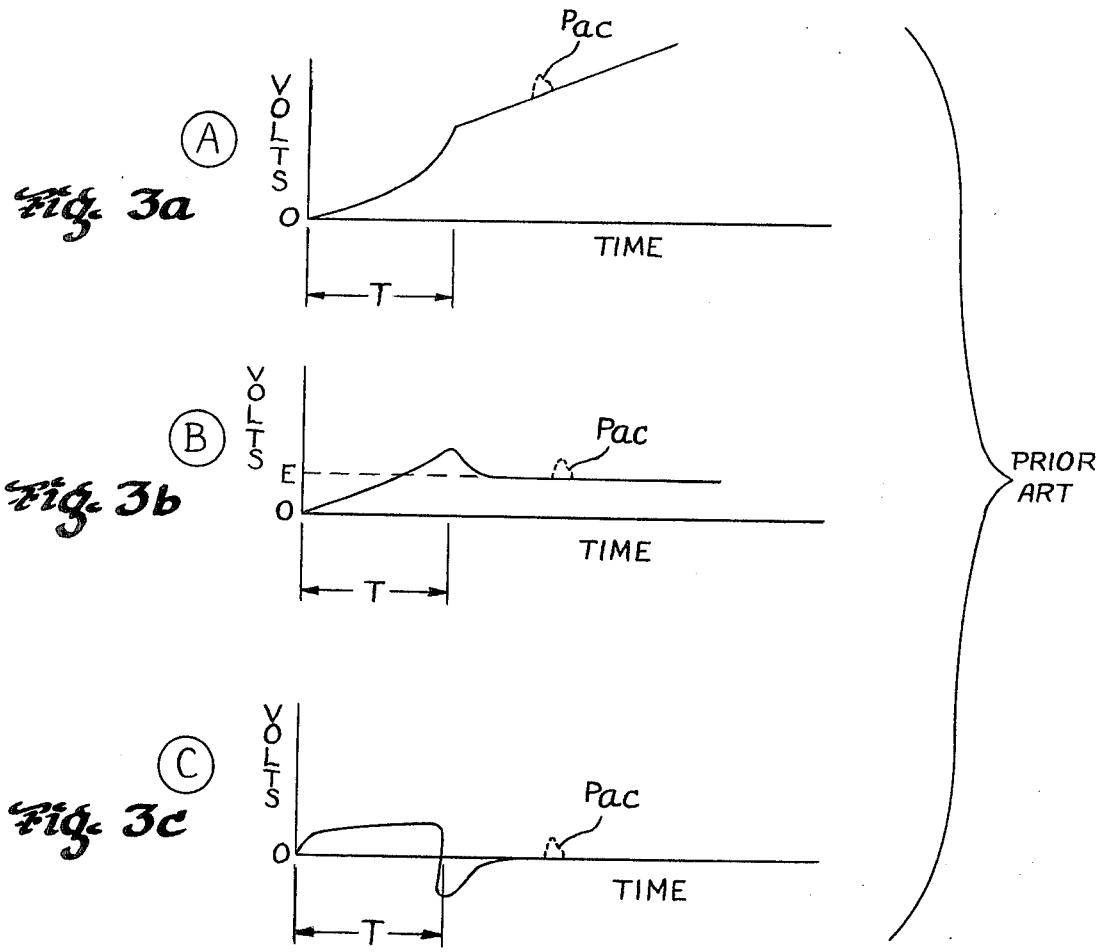
Fig. 3a
Fig. 3b
Fig. 3c
PRIOR ART

Haney

[11] 4,106,498
[45] Aug. 15, 1978

[54] INITIALIZATION CIRCUIT

[75] Inventor: Jerry D. Haney, Sunnyvale, Calif.

[73] Assignee: American Optical Corporation, Southbridge, Mass.

[21] Appl. No.: 754,486

[22] Filed: Dec. 27, 1976

[51] Int. Cl.² .............................................. A61B 5/02
[52] U.S. Cl. ................................. 128/2.05 A; 324/125
[58] Field of Search .................. 128/2.05 A, 2.05 C, 128/2.05 D, 2.05 E, 2.05 R, 2.05 T, 2.05 P, 2.05 M, 2.05 Q, 2.05 S, 2.06 A, 2.06 R, 2.1 R; 315/380, 381, 386; 324/102, 125; 73/430, 194 EM

[56] References Cited

U.S. PATENT DOCUMENTS

| 3,453,486 | 7/1969 | Weber .......................... 128/2.06 R X |
| 3,539,922 | 11/1970 | Brockman ........................ 324/102 X |
| 3,841,314 | 10/1974 | Page ............................ 128/2.05 A X |
| 3,859,602 | 1/1975 | Janssen et al. ................ 128/2.1 R X |
| 3,863,152 | 1/1975 | Wernite ........................... 324/125 X |
| 3,995,624 | 12/1976 | Maas ................................ 128/2.06 R |

FOREIGN PATENT DOCUMENTS 1,442,244  7/1976  United Kingdom .............. 128/2.06 R

OTHER PUBLICATIONS

Plumb, J. L. et al., "A Noise Suppressor for Neurophysiological Recording of Inpulse Activity," IEEE Trans, vol. BME-11, No. 4, Oct. 1969, pp. 157-159.

Primary Examiner—Robert W. Michell
Assistant Examiner—Francis J. Jaworski
Attorney, Agent, or Firm—Jeremiah J. Duggan; Stephen A. Schneeberger

[57] ABSTRACT

In a blood pressure measuring system in which a pressure signal comprised of both applied pressure and pulsatile pressure is detected and subsequently filtered to separate the pulsatile pressure component, circuitry is provided to minimize start-up transients in the separated signal. Such start-up transients, which normally persist for some time after start-up as a result of the AC time constants of the filters, are otherwise capable of generating erroneous measurements. The circuitry initializes the filters by clamping their outputs to predetermined voltage levels during a start-up interval and thereby avoids the generation of the transients.

9 Claims, 9 Drawing Figures

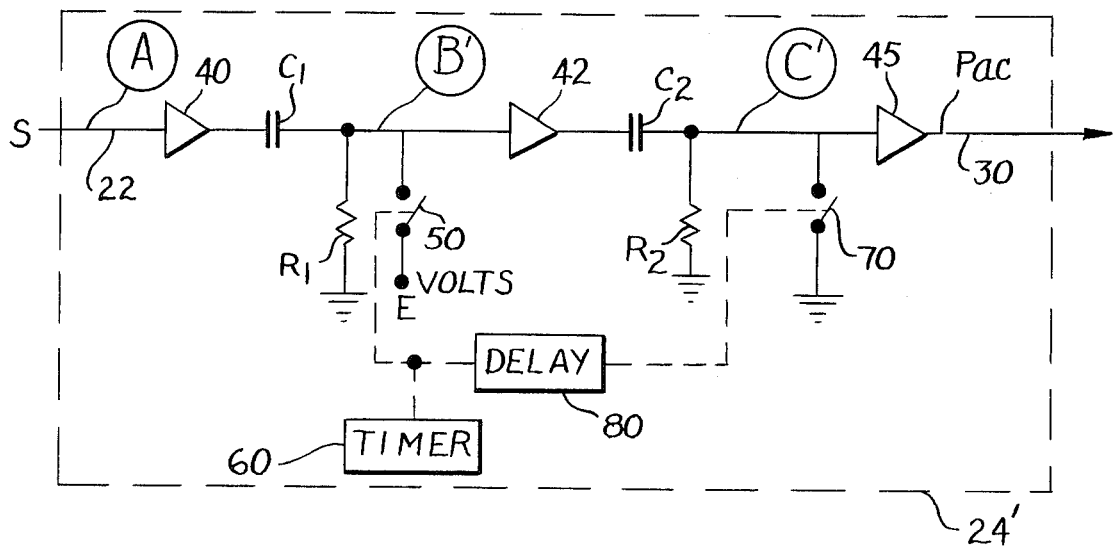

INITIALIZATION CIRCUIT

BACKGROUND OF THE INVENTION

The invention relates generally to blood pressure measuring equipment and to improvements therein.

The prior art is replete with devices for measuring the blood pressure of a living subject. An old and simple device is a pressurizable cuff used in combination with a mercury manometer which reads pressure in the cuff and a stethoscope which is used to listen to Korotkoff sounds. More complicated methods and apparatus using the same principle of listening to the Korotkoff sounds replace the mercury manometer with a mechanical or electromechanical pressure gauge and utilize microphonic detection of the Korotkoff sounds which are analyzed electrically.

Oscillometric methods for determining blood pressure are also well known in the art. In such methods, a representation of the strength of pulsations of pressure within an artery are observed either by an operator or by electronic signal processing means. Various techniques for determining blood pressure, systolic and/or diastolic, have been disclosed in U.S. Pat. No. 3,903,872 issued Sept. 9, 1975 to William T. Link for Apparatus and Process for Producing Sphygmometric Information, and in U.S. patent application Ser. No. 578,074 filed May 15, 1975 by Link et al for Apparatus and Process for Determining Systolic Pressure, which patent and application are respectively incorporated herein by reference.

The techniques disclosed in the aforementioned Link patent and Link et al patent application provide objective and relatively accurate means for the determination of diastolic and/or systolic blood pressure and utilize a signal obtained from a pressure cuff for the subsequent oscillometric waveform analysis. The signal obtained from the pressure cuff is representative of a sum quantity, S, comprised of the selectively changeable pressure, $P_{dc}$, applied by the cuff externally adjacent the blood vessel and a time dependent fluctuating component, $P_{ac}$, representative of the pulsatile pressure within the blood vessel. This sum quantity is analyzed in accordance with one or more predetermined algorithms for determining diastolic and/or systolic pressure within the blood vessel. In accordance with various preferred algorithms, particularly as disclosed in the aforementioned Link patent and Link et al patent application, the time dependent fluctuating component $P_{ac}$ or a time derivative thereof comprises the signal analyzed by the algorithm for determining diastolic and/or systolic pressure.

In those foregoing instances in which the fluctuating component $P_{ac}$ of the measured sum quantity is utilized by the analytical algorithm, it is generally required that the fluctuating component $P_{ac}$ be separated by a filter network from the sum value S for the purpose of the subsequent analytical determination. This separation may in fact comprise a first time differentiation of the fluctuating component and indeed even a second time differentiation in certain instances where required. Thus, it will be appreciated that such time differentiations of the fluctuating signal $P_{ac}$ may be accomplished by filtering networks having predetermined AC time constants which also serve to separate the $P_{ac}$ component from the sum quantity S.

During start-up of the blood pressure measuring apparatus various transient signals may be generated which, due to the AC time constants of the filter networks and other preceding circuitry, may continue to exist even after completion of the start-up interval. These transient signals may have AC characteristics similar to those of the $P_{ac}$ fluctuating signal which comprises the principle informational input to the analytical processing circuitry, and thus may distort the informational input during the early stages of a blood pressure measurement run.

Accordingly, it is a principle object of the invention to provide new and improved blood pressure measuring apparatus.

It is a further object of the invention to provide new and improved blood pressure measuring apparatus which minimizes erroneous pressure data readings during and shortly after start-up conditions.

SUMMARY OF THE INVENTION

In accordance with the invention, means are provided for minimizing and/or substantially eliminating the effects of start-up transients on the signal analyzing circuitry of a blood pressure measuring apparatus. The invention is particularly suited to blood pressure measuring apparatus which employ means such as a pressure cuff for applying a selectively changeable pressure to the patient externally adjacent a blood vessel, and wherein a signal measured at the pressure cuff comprises a fluctuating quantity proportional to a sum, the sum comprising a time-dependent fluctuating component representative of the pulsatile pressure within the blood vessel, plus the selectively changeable pressure applied externally adjacent the blood vessel, and wherein filter means having an AC time constant are utilized for at least separating the fluctuating component from the sum quantity for processing the fluctuating component by analytical signal processing means.

According to the invention, means are provided for initializing the filter means during start-up of the blood pressure monitoring apparatus, which initializing means comprises means for temporarily applying a predetermined potential to the filter means during at least the latter portion of the start-up interval and for removing the predetermined potential substantially at the end of the start-up interval. The DC output level of the filter means is a predeterminable value at the steady-state conditions following a start-up interval and accordingly, the predetermined potential applied to the filter means corresponds substantially with the predeterminable steady-state DC output from the filter means.

More specifically, the filter means may comprise first and second resistance-capacitance networks, with the capacitance means in each such network being in series arrangements, the capacitance of the first network being to reject low frequencies from the sum quantity and the resistance of the second network being to reject low frequencies from the output of the first resistance-capacitance network in order to minimize any DC offset. In such a two-filter network, a first predetermined potential is applied at the output side of the capacitance of the first network and a second predetermined potential is applied at the output side of the second network. Where the applied pressure is programmed to vary as a linear ramp, the first predetermined potential will be a function of the slope of the pressure ramp and the second predetermined potential will be substantially zero or ground reference. Further still, the second predetermined potential applied to the output of the second filter network is removed following a predetermined brief interval after removal of the first predetermined potential from the output of the first filter network.

BRIEF DESCRIPTION OF THE DRAWINGS

FIG. 1 illustrates a generalized block diagram of blood pressure monitoring apparatus including filter circuitry in accordance with the prior art;

FIG. 2 schematically illustrates in greater detail typical prior art filter circuitry as used in the blood pressure measuring apparatus of FIG. 1;

FIG. 3a is a plot of the voltage vs. time relationship of the signal appearing at the input to the filter circuitry of FIG. 2;

FIG. 3b is a voltage vs. time plot of the signal appearing at the output of the first filter stage of FIG. 2;

FIG. 3c is a voltage vs. time plot of the signal appearing at the output of the second filter stage illustrated in FIG. 2;

DETAILED DESCRIPTION OF THE PREFERRED EMBODIMENTS

Figure 4:
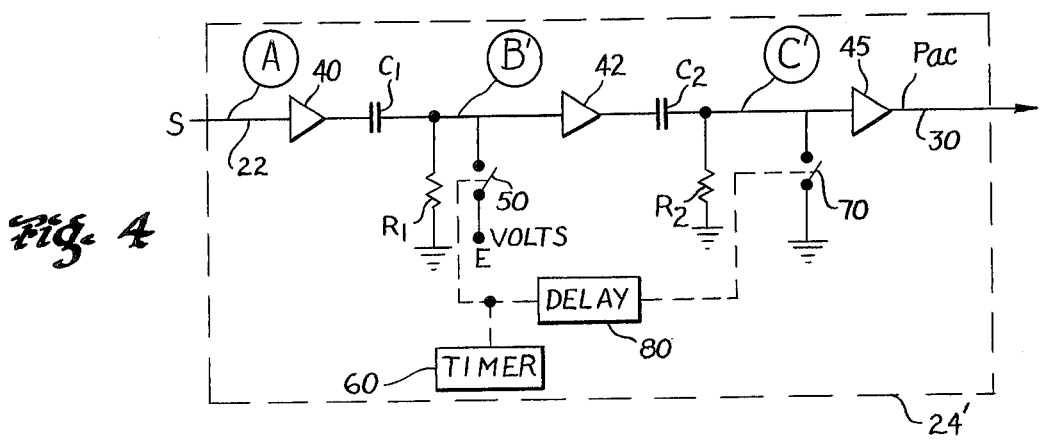
FIG. 4 illustrates the initialization circuitry of the invention in combination with the filter circuitry previously illustrated in FIG. 2.

Referring now to the figures and in particular FIG. 1, there is illustrated, in generally diagramatic form, blood pressure measuring apparatus of a known type. Means for applying a differable pressure adjacent a blood vessel, said pressure applying means comprising a blood pressure measuring means, in particular cuff 10 is shown in position about an arm 12 containing an artery 14 therein. The cuff 10 can be a typical blood pressure cuff such as those utilized when one is making use of a stethoscope to hear Korotkoff sounds. Also a part of the pressure applying means along with the cuff 10 is the pressurizing device 16 which may include a pump and/or release valve and appropriate controls therefore (not shown). The pressurizing device 16 might alternatively be a simple rubber bulb. In any event, the pressurizing device applies a selectively differable pressure to the cuff 10 via tubing 18 for selectively controlling the occlusion of the artery 14 embraced there within. The pressure resulting in the cuff is the sum of the pressure supplied by the pressurizing device 16 and a pulsating pressure due to the time dependent pulsatile pressure surges within the artery. The cuff pressure is measured by the pressure transducer 20 or by other convenient means.

The output of the pressure transducer 20 comprises a sum signal S appearing on line 22, the signal being representative of the pressure in the cuff and comprising the applied pressure component $P_{dc}$ plus the pulsatile pressure component $P_{ac}$. The sum signal S is extended to the input of filter circuitry 24 for separating the fluctuating component $P_{ac}$ from the sum signal and is additionally extended to an input of the signal processing means 26 for recording the applied pressure corresponding with $P_{dc}$. The signal processing means 26 includes storage circuitry and decision logic and, although implementable with discrete analog and/or digital circuitry, is preferably embodied by a digital microprocessor or the like.

The signal processing means 26 operates in accordance with the teachings of one or more of the aforementioned U.S. patent to Link and the U.S. patent application to Link et al, as well as other similar blood pressure analytical circuits to provide an indication of diastolic and/or systolic blood pressure of the patient as a function of the pulsatile component $P_{ac}$ of the sum signal S. For instance, signal processing means 26 may analyze the $P_{ac}$ component of the sum signal S to determine when the peak-to-peak value of the $P_{ac}$ signal is a maximum and to then determine the applied pressure $P_{dc}$ at which the peak-to-peak value of $P_{ac}$ is substantially one half the maximum $P_{ac}$ peak-to-peak value at an applied pressure greater than that at which maximum $P_{ac}$ peak-to-peak pressure occurred. The applied pressure so determined corresponds substantially with the patient's systolic pressure. Accordingly, it will be noted that the systolic pressure was determined in that instance as a direct function of $P_{ac}$.

In another instance, that disclosed in the U.S. Pat. No. 3,903,872 to Link, the first time derivative of the $P_{ac}$ signal may be obtained, either in filter circuitry 24 or in the signal processing means 26, and the signal processing means subsequently maximizes the first time derivative of $P_{ac}$ and indicates the corresponding applied pressure $P_{dc}$ as being the patient's diastolic pressure. In that instance it will be appreciated that the signal processing means 26 similarly analyzed a function $f(P_{ac})$.

It will be appreciated that additional and/or alternative algorithms may be incorporated in the signal processing means 26 for determining diastolic and/or systolic and/or other blood pressures in alternate manners. The blood pressure(s) so determined by signal processing means 26 are recorded and/or displayed on any suitable output device 28.

Referring back to filter circuitry 24, shown in greater detail in FIG. 2, the fluctuating component $P_{ac}$ of the sum quantity S is representative of the pulsatile pressure within the blood vessel and accordingly contains the information to be analyzed by signal processing means 26. Inasmuch as the waveform analysis performed by signal processing means 26 is essentially only on a signal which is a function of the pulsatile pressure i.e. $f(P_{ac})$, that component of the sum quantity S is separated from the sum signal by filter 24 and appears at the output thereof on line 30 which is extended to an appropriate input of signal processing circuitry 26. Typically, the cuff 10 is intended to apply a continuous, linear increasing or decreasing pressure ramp to the arm 12 of the patient under study. Further, during the start-up period or interval of each blood pressure monitoring run, the pressurizing device 16 may undergo a brief period of rapid pressure increase followed either by a longer period of slower pressure increase if an up-ramp is to be used, or followed by a long pressure decrease if a down-ramp is to be used. In either event, there exists a rapid pressure change during this start-up interval which is followed by a much slower rate of pressure change for the remainder of the run. Typically the start-up interval may be from a fraction of a second to several seconds or more. During the rapid rise in applied pressure in the start-up interval, the $P_{dc}$ component of the sum signal S (by far the largest fraction of the sum signal) also rises at a rapid rate, as illustrated in part during start-up interval T in FIG. 3a.

The filter circuitry 24 serves to separate the fluctuating $P_{ac}$ signal component from the sum signal S, which signal S further includes the $P_{dc}$ component representative of the relatively slowly changing pressure ramp. In the embodiment illustrated in FIG. 2, filter circuitry 24 comprises a two stage filter, the first stage being utilized to reject the low frequency components of the sum signal S substantially representative of the applied pressure $P_{dc}$ and the second stage being utilized to remove or minimize any DC offset resulting from and remaining after the filtering operation of the first stage.

More particularly, the sum signal S on line 22 is extended through an amplifier or buffer 40 to the input of a low frequency R-C filter comprised of the series capacitor $C_1$ and the resistor $R_1$ extending from the output of capacitor $C_1$ to ground. The waveform of the sum signal S appearing on line 22 is represented in the voltage vs. time plot of FIG. 3a.

Referring to FIG. 3a, the sum signal S is seen to undergo a rapid and generally exponential increase during the start-up interval T. This rapid increase is due to any one or more of the phenomena related to start-up of the blood pressure monitor and may include not only the rapid initial rise in the pressure $P_{dc}$ applied to cuff 10, but also the time constants of various circuit components, including amplifiers, appearing before the filter comprised of $R_1$ and $C_1$. It will be noted that at the end of start-up interval T, the sum signal S comprised principally of the applied pressure $P_{dc}$ proceeds as a linear, slowly rising ramp with the fluctuating component $P_{ac}$ representative of the pulsatile pressure shown superimposed thereon in dotted lines for purposes of illustration. The low frequency filter comprised of $R_1$ and $C_1$ serves to substantially separate the fluctuating component $P_{ac}$ from the applied pressure component $P_{dc}$ of the sum signal S, with the exception that the applied pressure is increasing with time and accordingly results in a DC offset of E volts, as illustrated in FIG. 3b. The FIG. 3b is a plot of voltage vs. time at the output of capacitor $C_1$ and accordingly, the output of the first filter stage. In this figure the exponential increase of sum signal S during start-up interval T now appears as a substantially linear, increasing ramp which, at the end of the start-up interval, slopes downwardly to the offset voltage E attained at steady-state conditions. The steady-state condition may be attained between a fraction of a second and several seconds following the end of the start-up interval, dependent upon the AC time constant of the $R_1 - C_1$ filter.

In order to remove the offset voltage E, the output of capacitor $C_1$ of the first filter stage is extended to the input of a second amplifier or buffer 42 having its output extended to the input of a second RC filter stage comprised of a series capacitor $C_2$ and a shunt resistor $R_2$ connected from the output of capacitor $C_2$ to ground. The filter $R_2 - C_2$ is similarly a low frequency filter and operates to remove the low frequency components in the output signal from the first RC filter as illustrated in FIG. 3b. Thus it is seen in FIG. 3c that the second filter $R_2 - C_2$ is operative to remove the DC offset of E volts from the steady-state portion of the signal appearing at the output of the first low frequency filter, thereby moving or shifting the signal base to a ground reference or 0 volts, with substantially the only variation therein during steady-state conditions being that of the pulsatile pressure fluctuating component $P_{ac}$.

However, it will be noted that during the start-up interval T, the output of filter $R_2 - C_2$ has some positive potential commensurate with the slope of the signal appearing during that same interval in FIG. 3b. Furthermore, the down-slope in the signal appearing in FIG. 3b between the end of the start-up interval and the attainment of steady-state conditions is reflected in FIG. 3c at the output of filter $R_2 - C_2$ as a negative signal of significant magnitude which exists until the attainment of the steady-state conditions at some time between a fraction of a second and several seconds thereafter. As noted, the $P_{ac}$ component appearing during the steady-state period beginning shortly after the end of start-up interval T and continuing substantially to the end of the pressure measuring run comprises the only signal having an amplitude other than zero and is thus utilized as the $f(P_{ac})$ signal input from amplifier 45 via line 30 to the signal processing means 26. However, it will be noted that the signal illustrated in FIG. 3c representative of the output of filter $R_2 - C_2$ is not of substantially zero magnitude during and shortly after the start-up interval but in fact includes both positive and negative components which may be comparable in magnitude to the $P_{ac}$ signal components to be analyzed by processing means 26. The presence of these non-zero signals during the start-up interval and shortly thereafter create and promote the possibility that the signal processing means 26 may detect and analyze such non-zero signals as being indicative of $P_{ac}$ information, thereby introducing erroneous data into the algorithmic process.

Referring to FIG. 4, there is illustrated in accordance with the invention the filter circuitry of FIG. 2 additionally including initialization circuitry for preventing the appearance of possibly ambiguous fluctuating signals other than $P_{ac}$ signals at the output 30 of the filter circuitry. The filter circuitry incorporating the initialization circuitry is generally designated as 24' with the circuit elements therein which are identical to corresponding circuit element in FIG. 2 being identically numbered. A normally-open switch 50 is connected by one terminal to the output of the first filter stage at the output of capacitor $C_1$ and is connected by the other contact or terminal to a preconditioning voltage of E volts, where E volts correspond with the steady-state offset voltage E illustrated in FIG. 3b. The switch 50 for purposes of illustration and clarity is illustrated as an electromechanically actuated mechanical switch, however it will be appreciated that a solid state semiconductor switching device would be suitable and may normally be preferred.

The normally-open switch 50 is maintained in a closed state for the duration of the start-up interval T by; means of a timer 60. Typically, the timer 60 may be a counting circuit or the like which is preconditioned to release or open switch 50 at the end of the interval predetermined to correspond substantially with the start-up interval T. The timer 60 might additionally and/or alternatively be structured to respond to some signal phenomenon commensurate with the end of the start-up interval T for releasing the switch 50.

With switch 50 closed, the first filter $R_1 - C_1$ is disabled during the start-up interval T and is additionally preconditioned to the offset voltage E. When switch 50 is opened at the end of start-up interval T, filter $R_1 - C_1$ exhibits only a small transient effect illustrated in FIG. 5b since the starting voltage when the switch is opened is substantially the same as the steady-state voltage the filter will achieve. Thus it is seen in FIG. 5b that, with the exception of a small-amplitude transient signal essentially at the end of the start-up T, the only fluctuating signal which may be analyzed by signal processing means 26 is the $P_{ac}$ signal itself.

A second normally-open switch 70, similar to switch 50, has one terminal connected to the output of the second filter at the output of capacitor $C_2$ and has the other contact or terminal connected to a zero reference potential such as ground. Switch 70 is similarly controlled by timer 60, however a delay element 80 interposed in the control circuit between timer 60 and the switch 70 serves to delay the opening of the switch somewhat longer than that of switch 50. Delay element 80 may comprise any suitable means for delaying the opening of switch 70 until a short time after the opening of switch 50 and may in fact comprise an extension of the timer 60 or a monostable multivibrator or the like. By opening switch 70 a short time after the opening of switch 50, any small remaining transient appearing in the waveform illustrated in 5b, as at the end of the start-up interval T, is substantially eliminated, as seen in FIG. 5c. The small transient illustrated in FIG. 5b will be of inconsequential amplitude following an interval which is even less than interval between the end of the start-up interval and the attainment of steady-state condition as illustrated in FIG. 3b and may be on the order of a second or less.

Figure 5A:
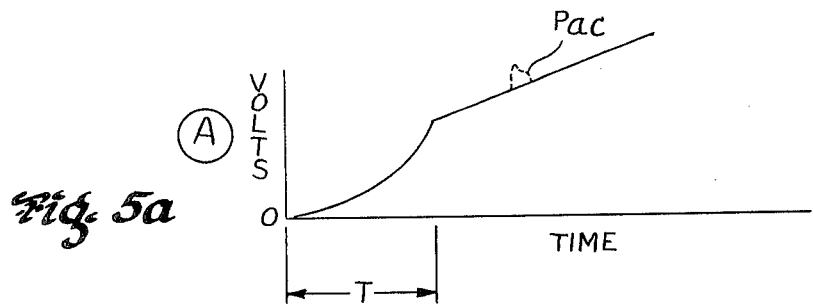
FIG. 5a is a voltage vs. time plot of the signal appearing at the input of the filter circuitry illustrated in FIG. 4.
Figure 5B:
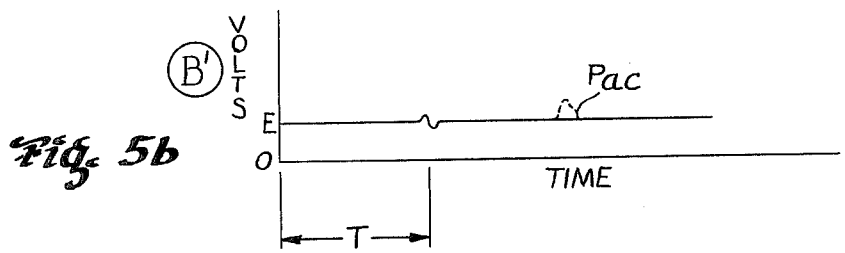
FIG. 5b is a voltage vs. time plot of the signal appearing at the output of the first filter stage illustrated in FIG. 4.
Figure 5C:
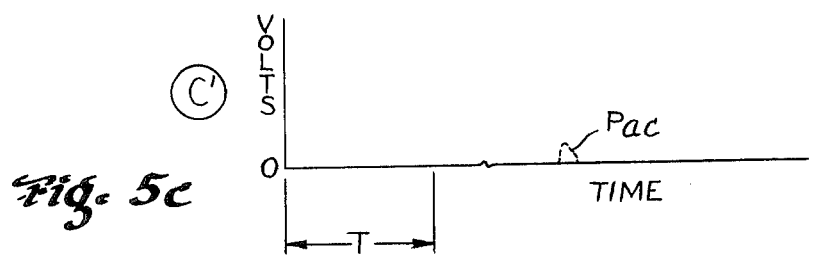
FIG. 5c is a voltage vs. time plot of the signal appearing at the output of the second filter stage illustrated in FIG. 4.

Thus it is seen that the initialization circuitry including switch 50 and potential E is operative with filter $R_1 - C_1$ to substantially eliminate the primary start-up transient illustrated in FIG. 3b, and the circuitry including switch 70 connected to ground is operative with filter $R_2 - C_2$ to substantially eliminate any remaining secondary transient illustrated in FIG. 5b.

It will be appreciated that the switch-applied potentials E and ground serve to disable the filters $R_1 - C_1$ and $R_2 - C_2$ respectively during (and in the latter, briefly after) the start-up interval to avoid the unwanted transmission of transients there through which might be mistaken as representing valid $P_{ac}$ values.

It should be further observed that although the time constants of the filters $R_1 - C_1$ and $R_2 - C_2$ in the illustrated embodiment were presumed to be such that the $P_{ac}$ component appearing in the sum signal S would undergo very little change in form as it passed through filter network 24, it would be possible, either additionally in the same apparatus or alternatively, to select R-C time constants which would result in a first and/or a second time differentiation of the $P_{ac}$ signal if it was that $f(P_{ac})$ which was to be utilized by processing circuitry 26. However, it will be appreciated that because the R-C time constants are shorter for obtaining the time derivative of $P_{ac}$, the problem of start-up transients may be correspondingly reduced.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. In an apparatus for measuring blood pressure of a patient, including means for applying a selectively changeable pressure to the patient externally adjacent a blood vessel, means for measuring a fluctuating quantity proportional to a sum, said sum comprising a time-dependent fluctuating component representative of the pulsatile pressure within the blood vessel, plus the selectively changeable pressure applied externally adjacent the blood vessel, filter means having an AC time constant for separating said fluctuating component from said quantity, the DC output level of said filter means being a predeterminable value at steady-state following a start-up interval, and an analytical means responsive to said fluctuating component from said filter means for providing an indication of the patient's blood pressure, the improvement comprising:

Means for initializing said filter means during start-up of said apparatus, said initializing means comprising means for temporarily applying a predetermined potential to said filter means during at least the latter portion of a start-up interval and for removing said potential substantially at the end of said start-up interval, said predetermined potential corresponding substantially with said predeterminable steady-state DC output from said filter means.

2. The apparatus of claim 1 wherein said filter means comprises a resistance-capacitance network, the capacitance of said resistance-capacitance network being in series arrangement to reject low frequencies from said quantity and said predetermined initializing potential being temporarily applied to the output side of said capacitance.

3. The apparatus of claim 2 wherein said filter means additionally comprises an other resistance-capacitance network, the capacitance of said other resistance-capacitance network being in series arrangement with the output of said resistance-capacitance network to reject low frequencies therefrom and thereby minimize DC offset, and wherein said initializing potential applying means further comprises means for temporarily applying an other predetermined potential to the output side of the capacitance of said other resistance-capacitance network and for removing said other predetermined potential therefrom following a predetermined brief interval after said removal of said first predetermined potential.

4. The apparatus of claim 3 wherein the steady-state output level of said other resistance-capacitance network following the start-up interval is substantially zero and said other predetermined potential is ground reference.

5. The apparatus of claim 1 wherein said predetermined potential remains applied to said filter means for a brief interval immediately following completion of the start-up interval.

6. The apparatus of claim 1 wherein said predetermined potential is applied to the output of said filter means substantially throughout said start-up interval.

7. An apparatus for measuring blood pressure of a patient comprising means for applying a selectively changeable pressure to the patient externally adjacent a blood vessel; means for measuring a fluctuating quantity proportional to a sum, said sum comprising a time-dependent fluctuating component representative of the pulsatile pressure within the blood vessel, plus the selectively changeable pressure applied externally adjacent the blood vessel; filter means having an AC time constant for separating said fluctuating component from said quantity, the DC output level of said filter means being a predeterminable value at steady-state following a start-up interval of the apparatus; means for initializing said filter means during the start-up of said apparatus, said initializing means comprising means for temporarily applying a predetermined potential to said filter means during at least the latter portion of the start-up interval and for removing said predetermined potential substantially at the end of said start-up interval, said predetermined potential corresponding substantially with said predeterminable steady-state DC output from said filter means; and analytical means responsive to said fluctuating component from said filter means for providing an indication of the patient's blood pressure.

8. The apparatus of claim 7 wherein said applied pressure changes at a different rate following said start-up interval than during said start-up interval, the rate-of-change of said applied pressure following said start-up interval being substantially constant and providing said predeterminable DC output level from the filter means.

9. The apparatus of claim 7 wherein said filter means comprises a first resistance-capacitance network and a second resistance-capacitance network, the said capacitance in each said first and second resistance-capacitance network being in series arrangement to reject low frequencies from said quantity and low frequencies from said first resistance-capacitance network respectively, said predetermined initializing potential comprising first and second predetermined potentials, said first predetermined potential being temporarily applied to the output side of the capacitance of said first resistance-capacitance network and the second predetermined potential being applied to the output side of the capacitance of said second resistance-capacitance network, said first predetermined potential having a value corresponding substantially with the predetermined DC offset value appearing at the output of said first resistance-capacitance network at steady-state and said second predetermined potential having a value corresponding substantially with ground reference potential.

* * * * *